United States Patent [19]

Hildon

[11] 4,325,888
[45] Apr. 20, 1982

[54] PREPARATION OF PERACID BY LIQUID-LIQUID EXTRACTION

[75] Inventor: Anthony M. Hildon, Tattenhall, England

[73] Assignee: Propylox, Brussels, Belgium

[21] Appl. No.: 151,817

[22] Filed: May 21, 1980

Related U.S. Application Data

[63] Continuation of Ser. No. 973,630, Dec. 27, 1978, abandoned.

[30] Foreign Application Priority Data

Jan. 13, 1978 [GB] United Kingdom ............... 01335/78

[51] Int. Cl.³ .......................................... C07C 179/10
[52] U.S. Cl. ............................................. 260/502 R
[58] Field of Search ..................... 260/502 R; 568/566

[56] References Cited

U.S. PATENT DOCUMENTS

| | | | |
|---|---|---|---|
| 2,048,820 | 7/1936 | Schmid ................. | 422/258 |
| 2,076,126 | 4/1937 | Guinot ................. | 422/258 |
| 2,361,780 | 10/1944 | Lewis ................... | 422/258 |
| 2,682,452 | 6/1954 | Wainwright ........... | 422/259 |
| 2,851,396 | 9/1958 | Myers ................... | 422/256 |
| 3,206,288 | 9/1965 | Hazen et al. .......... | 422/258 |
| 3,233,876 | 2/1966 | Faure et al. .......... | 422/258 |
| 3,374,988 | 3/1968 | Eckert .................. | 422/258 |
| 4,071,541 | 1/1978 | Hildon et al. ......... | 260/502 R |
| 4,160,778 | 7/1979 | Hildon et al. ......... | 260/502 R |
| 4,168,274 | 9/1979 | Hildon et al. ......... | 260/348.25 |

FOREIGN PATENT DOCUMENTS

| | | | |
|---|---|---|---|
| 885503 | 12/1961 | United Kingdom ............... | 422/259 |
| 1425077 | 2/1976 | United Kingdom . | |
| 428503 | 11/1974 | U.S.S.R. ............................. | 422/258 |

*Primary Examiner*—Werren B. Lone
*Attorney, Agent, or Firm*—Larson and Taylor

[57] ABSTRACT

The invention provides a process and apparatus for liquid-liquid extraction in which a first liquid phase is passed continuously through a series of extraction stages (10) while a second liquid phase is passed continuously through the series in counter-current to the first phase. In each stage the second phase is dispersed as by a sieve plate (11) and then allowed to coalesce into a settled body (14) from which the second phase is withdrawn and passed to the next adjacent stage. The invention is characterized by the fact that the flows of the two phases in each stage are generally transverse to each other. Preferably the first phase flows through the series of stages under gravity while the second phase is pumped (16) from stage to stage to control its interstage transfer.

The invention combines the features of separate control of residence time characteristics of an extraction column with the safety aspects inherent in a mixer/settler battery.

8 Claims, 4 Drawing Figures

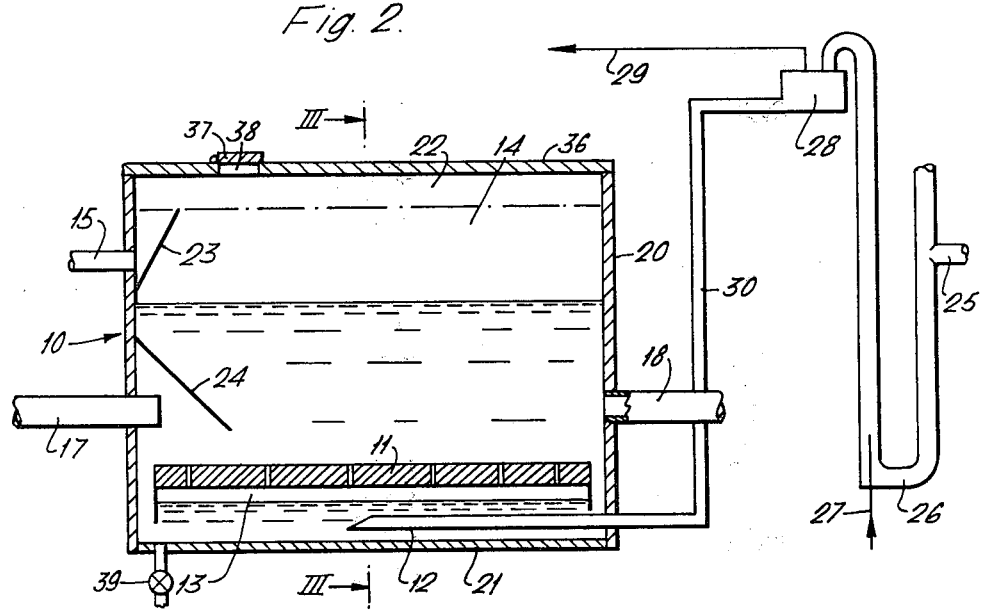
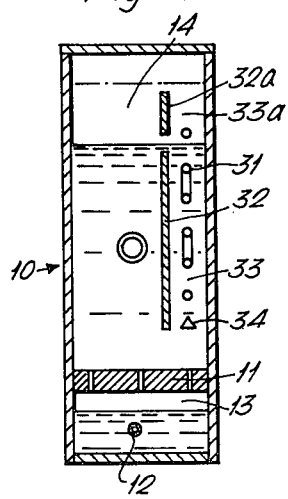
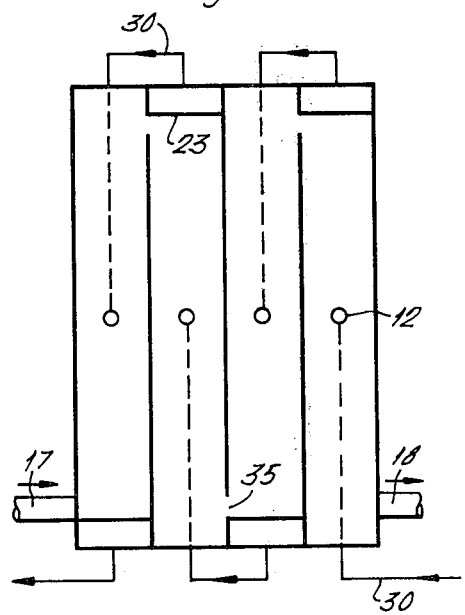

PREPARATION OF PERACID BY LIQUID-LIQUID EXTRACTION

This is a continuation of the application Ser. No. 973,630, filed Dec. 27, 1978, now abandoned.

BACKGROUND OF THE INVENTION

The present invention relates to a process and apparatus for contacting two immiscible liquid phases, for example in the organic extraction of an aqueous phase. The invention has particular, but not exclusive, relevance to, and will be described with respect to, the preparation of peracids (by which we mean herein peroxycarboxylic acids). The use of such peracids is well known in the epoxidation of alkenes, especially lower alkenes. Those skilled in the art of liquid-liquid extraction will readily understand what other processes the present invention can be applied to.

DESCRIPTION OF THE PRIOR ART

The general techniques of extraction of a substance from a first liquid phase with a second and immiscible liquid phase are well known. Normally such extraction is carried out using counter-current techniques. The two main classes of apparatus used are known as "extraction columns" and "mixer-settlers". One advantage of extraction columns is that different residence times can be used for the two phases but one disadvantage is that imperfect contacting of the two phases may occur due chiefly to non-uniform flow of the phases, particularly in large columns. One advantage of mixer-settlers is that efficient contacting is ensured. However in conventional mixer-settlers operating under steady state conditions, the residence times of the two phases are normally the same regardless of the relative rates of flow of the two phases, unless special recycling stages are provided.

An alternative technique is called cross-current extraction and is described in "Liquid-liquid Extraction" by L. Alders 2nd Ed. 1959, published by Elsevier Publishing Company. However for the reasons stated therein on page 66 this has severe defects and is described in "Chemical Engineers Handbook" by Robert H. Perry 5th Ed. published by McGraw-Hill Book Company at page 15—15 under the more appropriate name of "simple multistage contact".

SUMMARY OF THE INVENTION

It is an object of the present invention to provide a process and apparatus for liquid-liquid extraction.

According to the present invention, there is provided—a process for liquid-liquid extraction, comprising passing a first liquid phase continuously through a series of extraction stages, passing a second liquid phase continuously through said series in counter-current to the first phase and, in each said stage, effecting dispersal of the second phase in the first phase and allowing coalescence and separation of the second phase into a settled body from which the second phase is withdrawn and passed under control to the next adjacent stage as aforesaid, characterised in that the flows of the two phases in each stage are generally transverse to each other.

According to a further aspect of the present invention, there is provided a liquid-liquid extraction apparatus comprising a plurality of vessels arranged in a series, means to introduce a first liquid phase into the first vessel of the series and to cause or permit it to flow through the series, means to withdrawn the first phase from the last vessel of the series, means to introduce a second liquid phase into said last vessel, and means to withdraw the second phase from the first vessel of the series, dispersing means for said second phase in each of the vessels adapted to effect dispersal of the second phase throughout the first phase in each vessel, a space in each vessel permitting coalescence of said second phase, means for collecting such settled second phase and means for permitting or causing transfer of such collected second phase to the next adjacent vessel in the series for introduction thereinto, characterised in that the flows of the two phases in each stage are generally transverse to each other.

In the preferred arrangement, with all the vessels in a common horizontal plane, the first phase flows generally horizontally through each vessel and throughout the series whilst the second phase flows generally vertically in each vessel from the dispersing means, there being a single dispersal in each vessel. This arrangement must be clearly distinguished from "cross-current extraction" as above described since the flows of the two phases through the overall system are countercurrent. Pump means will normally be required to convey the second phase from vessel to vessel, the pump means also conveniently serving to control the transfer of the second phase from stage to stage.

Preferably, in accordance with common practice in conventional columns, the second phase (which forms the dispersed phase) is the phase having the larger volume passing through the apparatus in unit time. The difference in specific gravities of the two phases will determine whether the dispersed phase moves upwardly or downwardly in each vessel. Dispersion of the second phase may be effected by suitable dispersing means for example spray head, sieve plates, or the like, but it will be understood that the dispersion is not effected by a stirrer or the like in such a way as to prevent coalescence of the second phase which takes place in the same vessel and not in a separate vessel or compartment as is common in a "mixer/settler". Nevertheless each vessel may be provided with agitation means, for example a stirrer or sparge pipe, for use only under shutdown conditions. The dispersed phase may have its flow pulsed.

Application to preparation of peracids

The general preparation of peracids by the reaction of a carboxylic acid with hydrogen peroxide in an aqueous medium is well known. It is also known that such peracids can be extracted into organic solvents. One process for the preparation of peracids is disclosed in DOS No. 2602776 (GC36). An alternative process is disclosed in BP No. 1,425,077.

As previously mentioned, a well-known use of peracids is in epoxidation, and the present invention is particularly suitable for integration with such a process.

More specifically therefore a feature of the invention is that it can be used to extract a peracid into organic solution from an aqueous solution. Moreover the aqueous solution of the peracid may be generated in situ by supplying an aqueous solution of hydrogen peroxide in countercurrent to an organic solution of a carboxylic acid.

Comparison with the Prior Art

The most relevant forms of prior art are the conventional sieve plate column and the conventional mixer/- settler battery. In general the present invention can be considered to be a hydride between these two conventional extraction devices. Thus it behaves and can be controlled in much the same way as a sieve plate column but without suffering from the defects known to exist in sieve plate columns. On the other hand the physical disposition of the stages is similar to a mixer/settler battery with the known advantages of that arrangement but without the disadvantage of the restriction on residence time in a mixer/settler battery.

Thus if we compare the present process with the prior art, from a technical standpoint, upon the assumption that the peracid is perpropionic acid, and the solvent is propylene dichloride, these being the preferred compounds for reasons which will appear, the specific gravity of the aqueous phase is influenced by the concentration of sulphuric acid which also influences the rate of the reaction. The optimum concentration of sulphuric acid, with respect to the extent and rate of the reaction, gives a specific gravity to the aqueous phase which is so high compared with the organic phase that the depth of the organic phase below the plates in a conventional column is such that there is a risk of breakthrough of uncoalesced phases, unless the aperture size of the sieve plate is reduced to a value as to make the formation of a stable emulsion probable. These related problems are particularly pronounced in large diameter columns (cross-sectional area greater than 10 square meters) since, as is known in such columns which are used in large scale production, there is an increased risk of local maldistribution of the phases. Moreover with such large columns it is difficult to prevent streaming of the aqueous phase. It is therefore calculable that with the selected reactants it would be difficult to operate a large conventional column with the required degree of efficiency.

Moreover although in theory runaway decomposition of the peroxidic reactant and product is unlikely, nevertheless it is possible and the consequences of such a decomposition are such that severe damage to the plant might occur. Since there is a possibility of such decomposition, steps must be taken to control it and these steps are difficult and expensive on very large columns. Thus it will be known that it is difficult to remove heat generated within a column and difficult to dump the contents of a multiplate column rapidly. Moreover since decomposition inevitably leads to gas generation and this gas is constrained by high hydrostatic pressure, additional problems are posed.

Thus in the preferred apparatus of the present invention the arrangement is such as to ensure that in each vessel of the series, the organic phase is distributed by a sieve plate as efficiently as is reasonably practicable and that the droplets of organic phase can rise through the aqueous phase and coalesce to form a settled body of the organic phase resting above the aqueous phase. It will be apparent that this settled body can be arranged to be of any convenient depth which is not in general determined by the resistance to flow imposed by the sieve plate of the next higher stage, as happens in conventional columns. It is therefore possible to ensure that only settled phase is passed to the sieve plate in each stage. This transfer will normally be by a pump and is effected under control in such a way as to maintain a proper depth of settled phase in each vessel. Thus the above-described problems of hydrodynamic instability which are found in large conventional columns are minimised.

The effect of minimising the hydrodynamic instabilities is also inherently to minimise the risk of chemical instabilities which chiefly arise when phases have not had time to react and equilibrate in each stage. Nevertheless, should instability occur in the apparatus of the present invention, its effect will normally be confined to a single vessel since the generated gas cannot pass from vessel to vessel. It is therefore only necessary to isolate the vessel in which the malfunction takes place and if necessary the contents of that vessel can be dumped in known fashion. It will be appreciated that this is a much simpler, quicker and easier operation than dumping the entire contents of a conventional column.

Finally, it will be apparent that, unlike conventional mixer-settlers, the residence times of the two phases can be separately controlled. This is particularly advantageous where reaction takes place simultaneously with extraction.

The apparatus of the present invention is therefore capable of being designed so as to be easier to control, more efficient and safer than a conventional large diameter column. In this way the apparatus of the present invention closely resembles a battery of mixer-settlers but it achieves the desired technical result without incurring the disadvantages known in mixer-settlers.

Generalised Description of the Process

It will be apparent from the above that the present invention has particular advantage in extraction processes operating on a large scale; in processes in which there is a risk of chemical instability; in processes in which a chemical reaction takes place simultaneously with the extraction process; and in processes in which, for example due to large specific gravity differential, there is a risk of hydrodynamic instabilities. Such processes are conveniently exemplified by the reaction of hydrogen peroxide with carboxylic acids to generate peracids and their extraction into an organic solvent. The invention will therefore be particularly described with reference to such a process. The organic solution of a peracid is useful, for example, in the epoxidation of an alkene to give an oxirane or epoxide and such end use will be envisaged in the description of the process. It will be appreciated that the process to be described uses an aqueous phase but it should be understood that two immiscible organic liquid phases could also be used in the invention.

Selection of the carboxylic acid

As used herein, the term "carboxylic acid" has its normal meaning but it is necessary to emphasise that in practising the invention a proper selection of the "carboxylic acid" and "organic solvent" is desirable in order to provide optimum efficiencies. However with the guide lines given herein such selection is within the ability of one skilled in the art. It is clearly necessary to select a carboxylic acid which is sufficiently soluble in water to permit the reaction to take place and such that it and the peracid are also sufficiently soluble in the organic solvent to permit extraction to take place. Moreover the carboxylic acid and peracid should not undergo undesirable side reactions. For these reasons we prefer to use unsubstituted monocarboxylic acids having at least two but less than six carbon atoms.

The preferred carboxylic acids are acetic and propionic acids.

Selection of the solvent

The process to be described in detail is one in which the extraction into the organic phase takes place simultaneously with the reaction to form the peracid, but substantially the same criteria apply to separate reaction and extraction stages.

The prime function of the organic solvent is to provide a discrete organic phase in which the carboxylic acid and peracid are soluble. Additional desirable criteria for the organic solvent are a low solvent power for water, a low solubility in aqueous sulphuric acid and non-reactivity under the conditions of the reaction in the presence of the other reactants. It will be understood that although various solvents are listed herein, the selection of a solvent for practical use must depend on the precise process and reactants, and on the end use for the peracid.

The solvent may be a halogenated, e.g. fluorinated or chlorinated, aliphatic, cycloaliphatic or aromatic hydrocarbon for example:
dichloromethane, trichloromethane, tetrachloromethane,
chloroethane, 1,1-dichloroethane, 1,2-dichloroethane, 1,1,1-trichloroethane, 1,1,2-trichloroethane, 1,1,1,2-tetrachloroethane, 1,1,2,2-tetrachloroethane,
1-chloropropane, 2-chloropropane, 1,1-dichloropropane,
1,2-dichloropropane, 1,3-dichloropropane,
2,2-dichloropropane, 1,1,1-trichloropropane,
1,1,2-trichloropropane, 1,1,3-trichloropropane,
1,2,2-trichloropropane, 1,2,3-trichloropropane,
tetrachloropropanes, or chloro-substituted butanes, pentances or hexanes, cyclohexyl chloride or chlorobenzene.

Chlorinated hydrocarbons, although normally considered very inert, may give rise to chloride species, which in the presence of water and/or sulphuric acid can be very corrosive. It may therefore be desirable to select the solvent from among non-chlorinated hydrocarbons, such as aliphatic hydrocarbons, cycloaliphatic hydrocarbons, aromatic hydrocarbons and alkyl-aryl hydrocarbons for example:
decane, heptane, cycloheptane, benzene, toluene or xylene.

Other solvents, known generally in the art of peracids may be used.

A solvent mixture can be used, for example that known as petroleum ether which is a mixture of aliphatic hydrocarbons or mixtures of solvents mentioned individually above.

It is not necessary that the organic solvent should be a saturated compound provided that any unsaturation is not epoxidisable under the conditions of the process.

Of all the solvents listed herein, the most preferred are 1,2-dichloroethane (ethylene diochloride), 1,2-dichloropropane (propylene dichloride) and benzene.

Production of peracid

Before describing the plant of the present invention it is convenient to describe, in general terms, the reaction itself.

In the reaction an aqueous phase, comprising sulphuric acid, hydrogen peroxide and water, and an organic phase, comprising carboxylic acid and organic solvent, are passed to the counter-current extraction apparatus.

The components will partition between the two phases and, in the aqueous phase, the reaction of hydrogen peroxide with carboxylic acid to give peracid will be catalysed by the sulphuric acid. This reaction is normally slow to reach equilibrium but is accelerated by the extraction of the peracid into the organic phase.

In addition to its function as catalyst, the sulphuric acid also has the function of adjusting the specific gravity of the aqueous phase to assist separation of the phases. The relative specific gravity of the organic and aqueous phases will determine their direction of movement in separation after admixture. However care should be taken, as is known, that the concentration of the sulphuric acid is maintained so as to be sufficient for catalysis but insufficient to cause degradation of any of the organic components by dehydration, etc. Optimisation of the sulphuric acid concentration on chemical and extraction criteria tends to lead to relative densities, plate dimensions, residence times, etc which are difficult to handle in conventional apparatus but which pose few problems in the apparatus of the present invention.

The aqueous solution removed from the extraction device has, in effect, had some or all of its hydrogen peroxide replaced by water. It is therefore desirably concentrated by the removal of water and recycled after addition of hydrogen peroxide.

Production of peracid-general conditions

Dealing with this part of the invention in more detail and as applied specifically to the preparation of perpropionic acids, using propylene dichloride as the organic solvent, an aqueous phase is supplied to the extraction device to pass therethrough. This aqueous phase comprises sulphuric acid, hydrogen peroxide and water. The proportion of sulphuric acid is desirably between 30% and 60% by weight and is preferably approximately 40% by weight. Conveniently for operating reasons the sulphuric acid is derived from 75% by weight sulphuric acid solution in water which forms a feedback from the purification stages which will be described hereinafter, together with make-up acid. The hydrogen peroxide is conveniently between 10% and 35% by weight of the aqueous phase and in practice 29% is very satisfactory. This hydrogen peroxide is very conveniently supplied as approximately 70% by weight solution in water.

Water makes up the third component of the aqueous phase and its proportions can readily be found by difference.

The organic phase is fed into the extraction device to pass in counter-current with the aqueous phase and comprises, for the production of perpropionic acid, a solution of propionic acid in propylene dichloride. The concentration of the propionic acid is preferably between 15% and 30% of the organic phase and desirably 20%.

The relative volume of the aqueous and organic phases passing through the apparatus in unit time and their concentrations together set the ratio between hydrogen peroxide and propionic acid. This ratio may be from 1:0.5 to 1:4 by moles but is conveniently about 1:1.4, the stoichiometrical ratio being 1:1.

It may be convenient to carry out a further extraction of the aqueous phase leaving the extraction device using fresh organic solvent in order to extract substantially all of both propionic acid and perpropionic acid from the aqueous effluent. It may also be convenient to effect a back-wash operation on the organic phase in order to remove dissolved hydrogen peroxide. This latter can be effected by dividing the aqueous feed to the device into two portions, one being primarily dilute sulphuric acid and the other primarily hydrogen peroxide, and introducing these two portions at spaced locations in the device.

Similarly the hydrogen peroxide feed can be divided into two or more portions introduced at spaced locations.

The reaction proceeds naturally at a satisfactory rate so that operation at natural temperatures is satisfactory. Natural temperature is to some extent dependent on a scale effect since only little heat is evolved on mixing and reaction. Since the reaction is not markedly temperature sensitive no special steps are needed and a temperature of 0°–30° C. is satisfactory.

As a guide to the election of a reactant/solvent system for the production of the peracid, reference should be made to Table 1 which shows some relevant data.

TABLE I

|  | pK × $10^5$ | Boiling point °C. | Density g/cc | Solubility in water |
|---|---|---|---|---|
| Carboxylic acids |  |  |  |  |
| formic | 17.7 | 101 | 1.22 | ∞ |
| acetic | 1.8 | 118 | 1.04 | ∞ |
| propionic | 1.3 | 141 | 0.99 | ∞ |
| n.butyric | 1.5 | 163 | 0.96 | ∞ |
| caproic | 1.4 | 205 | 0.93 | δ |
| n.heptoic | 1.3 | 223 | 0.92 | δ |
| chloracetic | 140 | 189 | 1.28 | v |
| α-chlorpropionic | 147 | 186 | 1.28 | ∞ |
| β-chlorpropionic | 10 | 204 | — | s |
| Solvents |  |  |  |  |
| chloroethane |  | 13.1 | 0.90 | δ |
| ethylene dichloride |  | 83.5 | 1.235 | δ |
| tetrachloroethane |  | 146 | 1.60 | δ |
| propylene dichloride |  | 96 | 1.16 | δ |
| chlorobenzene |  | 132 | 1.11 | i |
| cyclohexylchloride |  | 142 | 1.00 | i |
| trichlorethylene |  | 87 | 1.462 | δ |
| tetrachlorethylene |  | 121 | 1.623 | i |
| decane |  | 174 | 0.73 | i |
| heptane |  | 98 | 0.68 | i |
| cyclohexane |  | 81 | 0.78 | i |
| benzene |  | 80.1 | 0.88 | δ |
| toluene |  | 1110 | 0.87 | i |
| ethylacetate |  | 77 | 0.90 | s |
| ethyl propionate |  | 99 | 0.89 | δ |
| nitrobenzene |  | 211 | 1.20 | δ |
| di n-propyl ether |  | 91 | 0.74 | δ |
| petroleum ether |  | 80–100 | 0.8 | i |

Notes to TABLE I
1. The pk figures are for aqueous solution at 25° C.
2. The symbols for solubility are taken from Handbook of Chemistry and Physics; The Chemical Rubber Co; 46th Ed.

DESCRIPTION OF THE PREFERRED EMBODIMENT

Figure 1:
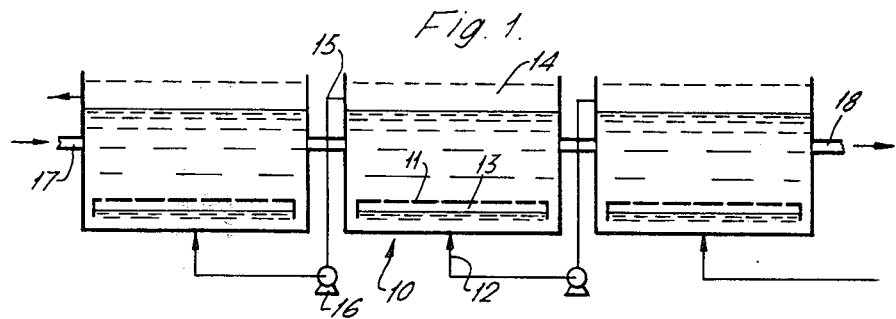
Figure 5:
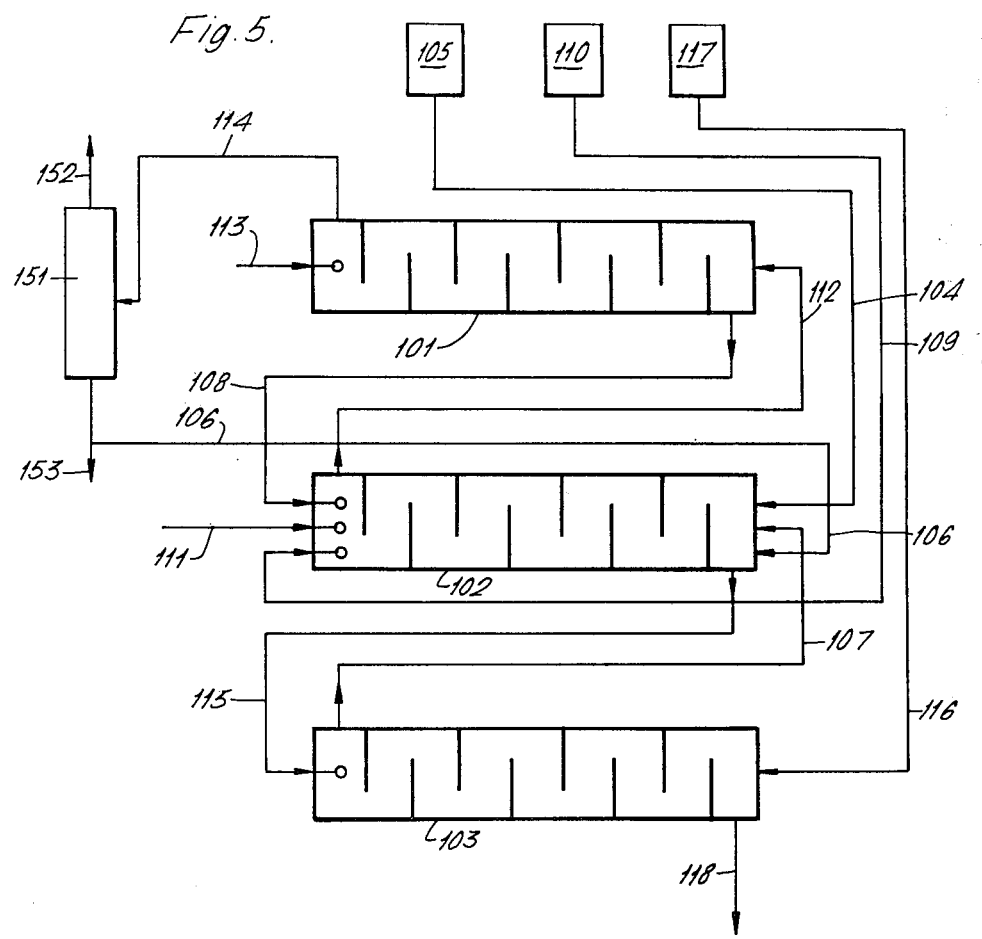

In order that the invention may more readily be understood one embodiment of the same will now be described by way of example and with reference to the accompanying drawings, wherein:

FIG. 1 illustrates the general concept,
FIG. 2 is a side elevational section of a single cell,
FIG. 3 is a section through the cell in FIG. 2 taken on the line III—III of FIG. 2,
FIG. 4 is a top plan view showing an arrangement of four cells, and
FIG. 5 is a diagramatic representation of a complete peracid generator.

Referring firstly to FIG. 1 of the drawings, it will be seen that the plant comprises a series of individual cells each of which is equipped with a sieve plate 11 adjacent to the base and with an inlet 12 for organic phase located in such a position that organic phase collects at 13 below the sieve plate 11 in the conventional manner. The organic phase passes through the sieve plate 11 and collects as an upper organic layer 14 at the top of the cell. The organic phase is withdrawn from the layer 14 via an outlet 15 and is passed by a pump 16 to the next adjacent cell. Similarly each cell is provided with an aqueous phase inlet 17 and an aqueous phase outlet 18 so arranged that the aqueous phase passes through each cell of the series but in countercurrent with the organic phase, the outlet 18 of one cell being connected to the inlet 17 of the next cell, the movement of the two liquids in each cell being transverse to each other.

FIG. 2 shows the arrangement of a single cell in greater detail. It will be seen that the cell comprises a conventional tank 10 having side walls 20 and a base 21, the tank having a lid 36 to prevent accidental ingress of material and a freely opening cover 37 to a vent 38 so that effectively there can be no build-up of pressure in the cell. There is a free space 22 between the lid 36 and the upper surface of the liquid in the cell. The upper level of liquid within the cell 10 is defined by a weir 23 which is arranged to guard the organic phase outlet 15 and ensure firstly that the level of liquid within the cell 10 is maintained correctly and secondly that only organic phase passes out of the outlet 15. Unless the geometry otherwise makes it unneccessary, it may be convenient to have a baffle 24 arranged adjacent to the aqueous phase inlet 17 in order to prevent streaming of the aqueous phase from the inlet 17 to the outlet 18 without proper mixing within the cell. However we prefer if possible to arrange for the geometry of the cells to be such that adequate mixing is promoted by the cell design and no separate baffle is needed. It will be understood that the cell illustrated in FIG. 2 operates in exactly the same way as a single stage in a multiplate column but without the constraints imposed by adjacent plates. Thus for example in the construction of the present invention, the depth of the organic layer 13 below the sieve plate 11 does not have to be the same as the depth of the organic layer 14 at the top of the cell. Such variation is not generally possible in a conventional column.

It will be seen from FIG. 1 that the aqueous phase flows from cell to cell without requiring any inter-cell pumping. The organic phase however overflows from the top of one cell and requires to be pumped in order to introduce it into the base of the next cell. Although conventional mechanically or electrically driven pumps could be used, the power requirements are so small that it is possible to use alternative forms of pump. The form that we prefer is known as a gas lift pump and is illustrated in FIG. 2. Organic phase enters the pump through a side limb 25 coupled to the outlet 15 of the previous stage and enters the open limb of a U-tube 26. The second limb of the U-tube 26 contains a gas injector 27 which forces a gas/liquid mixture up to a disengaging chamber 28. The gas is separated in the disengaging chamber 28 and is taken away by a line 29 for recycle, whilst the organic liquid flows by gravity down a pipe 30 to the inlet 12. A suitable gas for the gas lift is nitrogen. It will be apparent that the efficiency of the operation of the gas lift as a pump depends upon the level of the liquid in the U-tube 26 and this in turn depends upon the rate of overflow over the weir 23 of the preceding stage. The system is therefore inherently self-compensating.

In the event that the plant has to be shut down for any reason, there will be a tendency for a continuing reaction to take place in the individual cells which could overheat since there is no flow of liquid through them under shut down conditions. If the design is such that it is desirable to remove this heat and therefore reduce the tendency to runaway reaction, each of the cells may be equipped with a helical cooling coil and a stirrer. Under normal operation of the cells the stirrer will be inoperative and the coil ineffective. However under shut down conditions coolant is supplied to the coil and the stirrer is activated so that each cell is effectively converted to a cooled, stirred tank.

FIG. 3 illustrates an alternative arrangement in which coolant tubes 31 are located adjacent to one wall of the cell as a vertical bank with adjacent vertical baffles 32 and 32a which define, with the side wall of the cell, vertical cooling channels 33 and 33a for the aqueous and organic phaes respectively. These cooling channels 33 and 33a terminate as is shown, below the upper surfaces of each liquid phase. If additional flow through the channel is required in place of the downwards thermosiphon effect, gas, for example the nitrogen or other gas used in the gas lift pumps, can be supplied to a sparge pipe 34 at the base of the coolant channel 33. It will be appreciated that under shut down conditions the gas lift pumps are inoperative. If dumping of the contents of any selected vessel is necessary, this can be effected through operation of a dump valve 39.

An alternative construction to FIG. 1 which obviates the need for the baffle 24 shown in FIG. 2 is illustrated in FIG. 4, the sieve plates being omitted for clarity. In this arrangement, the cells are located side by side and are, comparatively speaking, long and thin. The organic phase moves as indicated through the pipes 30 (the pumps not being shown), whilst the construction is such as to cause the aqueous phase to flow in a sinuous manner through the series of cells, the inlets and outlets 17, 18 being replaced by apertures 35. Thus from the point of view of the aqueous phase, the arrangement can be considered as a plug flow reactor. It will readily be seen by reference to FIG. 4 that the flow of aqueous phase can be controlled by the simple expedient of controlling the flow from the final stage in accordance with an interface controller on the first stage. As previously explained, the arrangement of weirs and gas lift pumps inherently controls the organic phase. It will also be understood that, as in a column, the residence times of the two phases need not be the same. In this way the plant of the present invention differs very markedly from the mixer-settler arrangement.

A suitable arrangement for a complete plant is illustrated in FIG. 5. Purely by way of example the plant has been illustrated as having 27 separate cells arranged in three series but it should be understood that one or two of these series may be replaced by one or more conventional columns generally as described in the said DOS. The plant illustrated in FIG. 5 is intended for use with an epoxidation plant to which it supplies a solution of peracid in organic solvent and from which it receives separate recycle streams of carboxylic acid in organic solvent and or organic solvent. More specifically the plant illustrated in FIG. 5 is intended for the manufacture of perpropionic acid, using propionic acid as the carboxylic acid, and using propylene dichloride as the solvent.

The three series of cells are arranged to operate in series and in countercurrent. The main reaction takes place in the centre series of cells, conveniently called the "reaction stage" 102.

Aqueous hydrogen peroxide is supplied to the right hand of the reaction stage 102 by means of a line 104 from a hydrogen peroxide storage tank 105. Aqueous sulphuric acid is also supplied to the right hand end of the reaction stage 102 by a line 106, being in fact a recycle phase as will be apparent hereinafter.

Aqueous sulphuric acid is also supplied to the right hand end of the reaction stage 102 by a line 107 from the left hand end of the acid backwash stage 103. The hydrogen peroxide, sulphuric acid and water supplied by the lines 104, 106 and 107 together constitute the aqueous phase. An organic solution of propionic acid in propylene dichloride is supplied to the left hand end of the reaction stage 102 by a line 108 from the right hand end of the organic backwash stage 101. Fresh propionic acid in propylene dichloride from a make-up storage tank 110 is also supplied to the left hand end of the stage 102 by a line 109. Finally a recycle phase comprising propionic acid in propylene dichloride is supplied to the left hand end of the reaction stage 102 by a line 111. The propionic acid and organic solvent provided by lines 108, 109, and 111, to the left hand end of the reaction stage 102, together constitute the organic phase. The organic and aqueous phases pass through the stage 102 in counter-current flow and will react to produce perpropionic acid, which is extracted into the organic phase.

Thus an aqueous solution comprising sulphuric acid and water is taken from the left hand end of stage 102 by a line 112 and is taken to the right hand end of the organic backwash stage 101. Solvent, substantially free of propionic acid, is supplied to the left hand end of the stage 101 by a line 113 and passes in counter-current to the aqueous solution in order to backwash it and strip from it as much propionic acid as possible. The conditions are such that the aqueous effluent from the backwash stage 101 which is taken from the left hand end by line 114 contains substantially no propionic acid, perpropionic acid or hydrogen peroxide.

The organic solution from the right hand end of the stage 102 comprises a solution of perpropionic acid in propylene dichloride and is taken by a line 115 to the left hand end of the stage 103 which acts as an aqueous backwash stage. The right hand end of the stage 103 is provided with fresh sulphuric acid in aqueous solution by a line 116 from a make-up tank 117, this sulphuric acid passing out of the stage 103 by the line 107. The function of this aqueous acid backwash is to strip the organic phase flowing through the stage 103 to remove from it as much of the unreacted hydrogen peroxide as possible.

The organic solution of perpropionic acid leaves the right hand end of the acid backwash stage 103 by a line 118 as product.

The aqueous solution taken from the left hand end of the organic backwash stage 101 by the line 114 is to be utilised at least in part as a recycle stream, but it will by appreciated that this aqueous solution contains too much water for direct recycle since the original hydrogen peroxide content has reacted to give water. The line 114 therefore leads to a distillation column 151 where the aqueous solution is distilled in order to provide a light fraction which is substantially water and which is taken off by a line 152 and passed to waste. The heavy fraction from the column 151 comprises sulphuric acid in water and could conveniently be redistilled in order to remove high boiling impurities which would otherwide accumulate in the aqueous phase. However in the preferred arrangement a bleed from the aqueous phase is taken from the heavy fraction from the distillation column 151 by a line 153 and the remainder is passed back by the line 106 to the right hand end of the stage 102.

The stages 101, 102 and 103 preferably operate at normal temperature, that is to say without any added heating or cooling, and under normal hydrostatic pressure. The column 151 operating in the recycle stream can conveniently operate at a temperature and pressure of 130° C. and 100 torr. respectively.

In a practical embodiment of the invention the apparatus was substantially identical to the FIG. 4 arrangement except that 6 cells or vessels were provided. Each cell was of length 5 meters and width 2.5 meters, the whole being arranged within a 15 meter shell. The height of each cell was 3.3 meters, the upper surface of the liquid being 2.6 meters from the base so as to give a free space of 700 mm. below the lid. The apparatus was made of grade 316 stainless steel. The sieve plates 11 were spaced 200 mm from the base 21, and were mounted on levelling feet in order to ensure that they were truely horizontal. Each plate had approximately 12,000 holes 3 mm in diameter and arranged on a 30 mm square pitch. Under normal operating conditions the interface between the aqueous and organic phases was 2.4 meters from the base of the apparatus so as to give a settled layer of organic phase of approximately 200 mm depth.

In order to emphasise the difference between this device and a mixer/settler battery, the designed residence time for the aqueous phase was 80 minutes per stage, giving a total residence time of 480 minutes whilst the designed residence of the organic phase was about 3 minutes per stage giving a total residence time of 18 minutes. Because of the relatively large settled organic phase the organic phase spent a larage part of its residence time out of contact with the aqueous phase and the total contact time was probably of the order of 10 minutes. However, the aqueous phase was in contact with the organic phase for substantially the same length of time as its residence time.

By scale up from a smaller plant, the steady state flows to the first vessel of stage 102 comprised, in tonnes per hour:
Hydrogen peroxide (100%): 8.1
Sulphuric acid (100%): 12.8
Water: 7.7

The total aqueous volume inflow was approximately 19 cubic meters per hour.

The aqueous outflow volume in line 112 was 18.6 cubic meters per hour, and comprised in tonnes per hour:
Hydrogen peroxide: 0.18
Sulphuric acid: 12.8
Propionic acid: 1.3
Perpropionic acid: 0.2
Water: 11.6

The organic inflow at 30 to the last vessel of the stage 102 comprised, in tonnes per hour,
Propionic acid: 26.2
Propylene dichloride: 96.7
Perpropionic acid: 0.16

The total organic volume inflow was approximately 110 cubic meters per hour. The organic outflow volume in line 115 was 112 cubic meters per hour and comprised, in tonnes per hour,
Perpropionic acid: 19.9
Propylene dichloride: 96.7
Propionic acid: 8.52
Hydrogen peroxide: 0.4

If the same reaction were to be carried out in a conventional sieve plate column this would require not less than 20 plates for 600 mm spacing, that is to say a column approximately 12 m high and approximately 4 m in diameter. Such a column would be difficult and expensive to construct and control.

I claim:

1. A process for the production of a per acid comprising passing a first liquid phase comprising an aqueous solution of hydrogen peroxide through a series of extraction stages; passing a second liquid phase comprising a solution of carboxylic acid in an organic solvent through said series of stages in countercurrent to the first phase; effecting, in each stage, dispersal of the second phase into the first phase, whereby a peracid is generated by reaction in aqueous phase between the carboxylic acid and hydrogen peroxide and is extracted into the organic solvent; allowing, in each stage, coalescence and separation of the second phase into a settled body; withdrawing the second phase from such settled body and passing it under control to the next adjacent stage, the flow of one of said first and second liquid phases in each stage being substantially vertical and the flow of the other of said liquid phases being substantially horizontal whereby the flows of the two phases in each stage are generally transverse to each other.

2. The process of claim 1, wherein a single dispersal and coalescence is effected in each stage.

3. The process of claim 1, wherein the first liquid phase flows through the series of stages under gravity.

4. A method according to claim 1 wherein the second phase is lighter than the first phase and wherein the second phase flows upwardly in each stage.

5. A method according to claim 1 wherein the second phase is heavier than the first phase and wherein the second phase flows downwardly in each stage.

6. A method according to claim 1 wherein a weir is provided in said settled body and wherein the second phase is withdrawn from said settled body after flowing over said weir.

7. A process for the extraction of a peracid, comprising passing a first liquid phase continuously through a series of extraction stages, said first liquid phase comprising an aqueous solution of a peracid; passing a second liquid phase continuously through said series of extraction stages in countercurrent to the first phase, said second liquid phase comprising a solvent for said peracid; effecting, in each said stage, dispersal of the second phase in the first phase to effect extraction of said peracid from said first phase into said second phase; allowing, in each said stage, coalescence and separation of the second phase into a settled body; withdrawing the settled second phase from such settled body and passing it under control to the next adjacent stage; withdrawing the first stage liquid and passing it under control to the next adjacent stage; the flow of one of said first and second liquid phases in each stage being substantially vertical and the flow of the other of said liquid phases being substantially horizontal whereby the flows of the two phases in each stage are generally transverse to each other; providing in each stage cooling means and agitating means inoperative under normal operation of the process; and, under shut-down conditions, actuating said agitating means to cause a forced flow of liquid over the cooling means to effect cooling of the first and second phases in each stage.

8. A process for the production of a peracid, comprising passing a first liquid phase continuously through a series of extraction stages, said first liquid phase comprising an aqueous solution of hydrogen peroxide; passing a second liquid phase continuously through said series of extraction stages in countercurrent to the first phase, said second liquid phase comprising a solution of a carboxylic acid in an organic solvent; effecting, in each said stage, dispersal of the second phase in the first phase to effect generation of a peracid by reaction in the aqueous phase between the carboxylic acid and the hydrogen peroxide and to effect extraction of the peracid into said second phase; allowing, in each said stage, coalescence and separation of the second phase into a settled body and passing it under control to the next adjacent stage; withdrawing the first stage liquid and passing it under control to the next adjacent stage; the flow of one of said first and second liquid phases in each stage being substantially vertical and the flow of the other of said liquid phases being substantially horizontal whereby the flows of the two phases in each stage are generally transverse to each other; providing in each stage cooling means and agitating means inoperative under normal operation of the process; and, under shut-down conditions, actuating said agitating means to cause a forced flow of liquid over the cooling means to effect cooling of the first and second phases in each stage.

* * * * *